United States Patent [19]
Belvedere

[11] Patent Number: 5,360,482
[45] Date of Patent: Nov. 1, 1994

[54] APPARATUS AND METHOD FOR DISPENSING RESIN COATED FIBERS

[76] Inventor: Paul C. Belvedere, 5824 Creek Valley Rd., Edina, Minn. 55435

[21] Appl. No.: 929,771

[22] Filed: Aug. 12, 1992

[51] Int. Cl.⁵ ............................................. B05C 3/02
[52] U.S. Cl. .................................. 118/404; 401/9; 401/10; 118/405
[58] Field of Search ............... 118/404, 405, DIG. 19, 118/DIG. 18, 419, 420; 433/215; 401/9, 10

[56] References Cited

U.S. PATENT DOCUMENTS

| | | | |
|---|---|---|---|
| 439,916 | 11/1890 | Whittlesey | 15/256.6 |
| 839,567 | 12/1906 | Emerson | 118/DIG. 19 |
| 874,287 | 12/1907 | Bayne et al. | 118/DIG. 19 |
| 1,009,731 | 11/1911 | Fisher | 118/DIG. 19 |
| 1,539,518 | 5/1925 | Schreiber | 118/DIG. 19 |
| 1,797,249 | 3/1931 | Truesdale et al. | 118/DIG. 19 |
| 1,897,122 | 2/1933 | Hartmann et al. | 118/DIG. 18 |
| 1,961,148 | 6/1934 | Herman | 118/DIG. 19 |
| 2,218,482 | 10/1940 | Reevely | 118/DIG. 18 |
| 2,351,110 | 6/1944 | Davidson et al. | 118/DIG. 19 |
| 2,846,705 | 8/1958 | Marz | 401/10 |
| 3,874,332 | 4/1975 | Meinel | 401/9 |
| 4,314,834 | 2/1982 | Feenstra et al. | 118/405 |
| 4,505,222 | 3/1985 | Holt et al. | 118/DIG. 19 |
| 4,569,079 | 4/1986 | Nundy | 118/DIG. 18 |
| 5,107,961 | 4/1992 | Schott et al. | 118/404 |

Primary Examiner—W. Gary Jones
Assistant Examiner—Brenda Lamb
Attorney, Agent, or Firm—Dorsey & Whitney

[57] ABSTRACT

An apparatus and method for impregnating fibers and/or dispensing impregnated fibers including a dispenser body with a resin containing cavity, a fiber supply for supplying fiber to be passed through the resin in the cavity and an impregnated fiber outlet for removing impregnated fiber from the cavity.

5 Claims, 2 Drawing Sheets

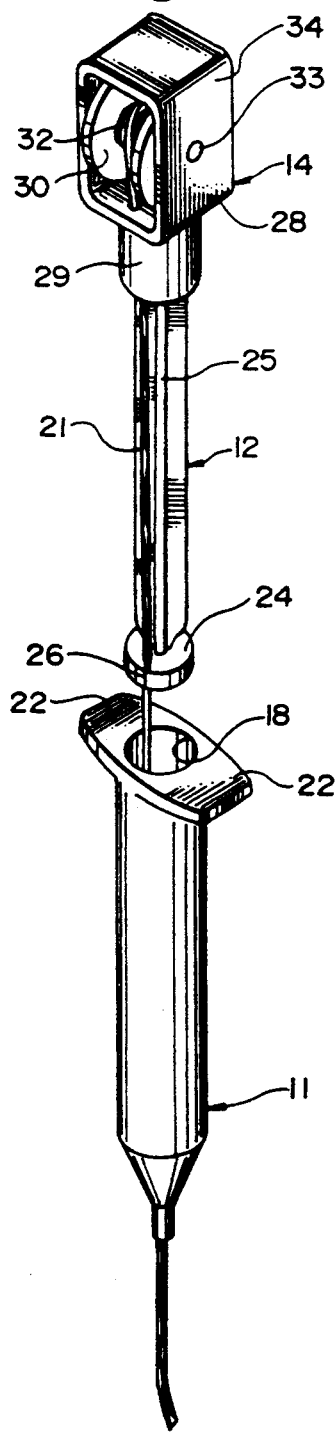
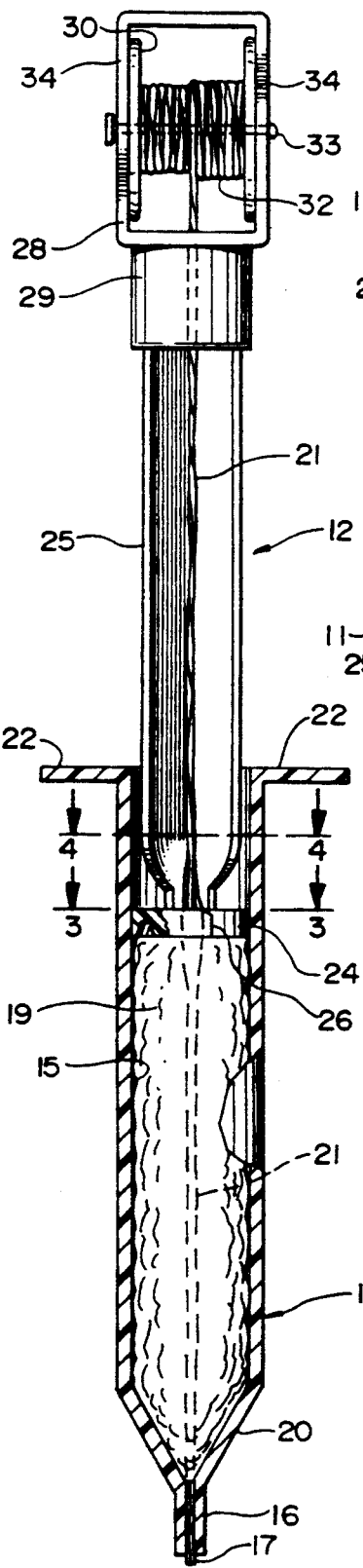
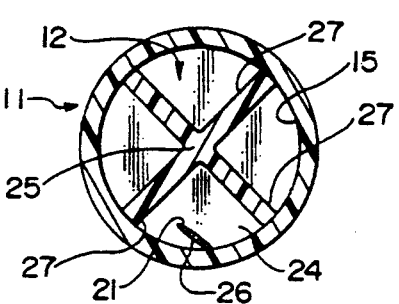
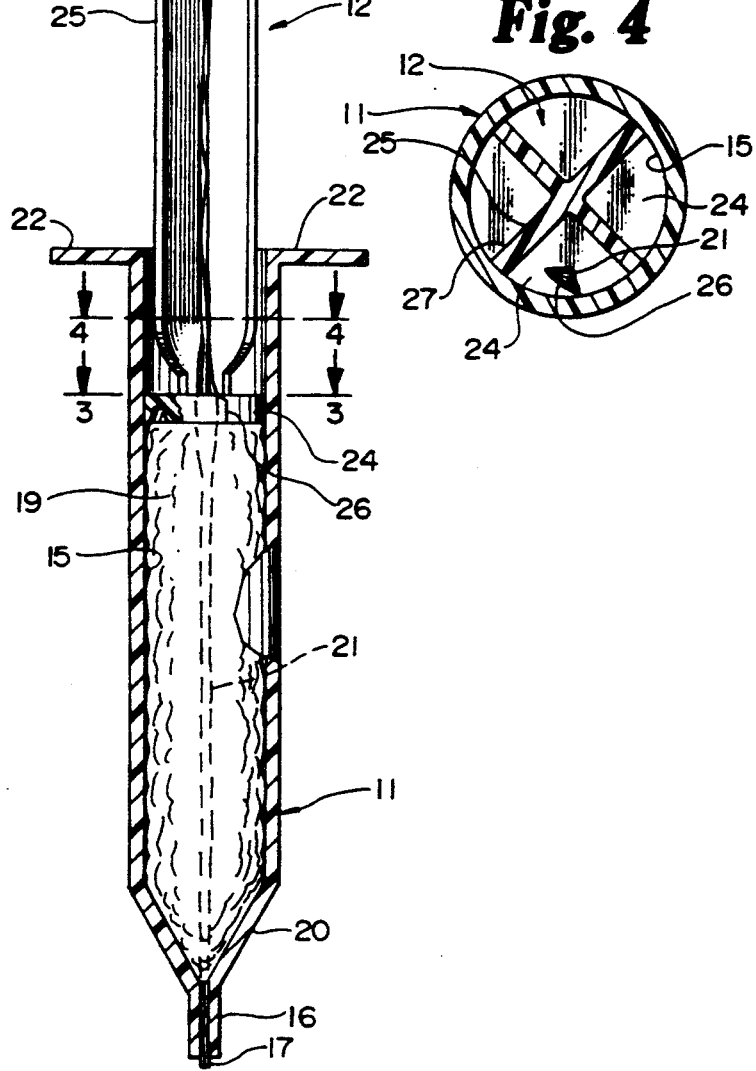

APPARATUS AND METHOD FOR DISPENSING RESIN COATED FIBERS

BACKGROUND OF THE INVENTION

1. Field of the Invention

The present invention relates generally to an apparatus and method for dispensing fibers, and more particularly, to an apparatus and method for dispensing resin coated or impregnated fibers or fiber bundles. The invention has specific application to the dental field and other fields where resin impregnated fibers or fiber bundles are needed or desired.

2. Description of the Prior Art

There are many fields of art in which fibers or fiber bundles impregnated with a resin or the like are needed or desired. The dental field is one such field.

In the dental field, procedures currently exist for using fibers, impregnated with a selectively curable resin, for various purposes such as the replacement of missing teeth and the splinting of mobile teeth without drilling, grinding or otherwise altering any of the abutment teeth. A procedure for replacing missing teeth involves preparation of the lingual surfaces of the abutment teeth, followed by application of an appropriate adhesive or bonding resin to these prepared surfaces. A plurality of reinforcing fibers or fiber bundles are then impregnated with a resin material. These resin impregnated fibers are laid across the gap from one abutment tooth to the other so that the fibers bridge or extend across this gap which will be filled by the artificial tooth or "pontic". The resin impregnated fibers are then appropriately activated or cured to secure the fibers to the supporting abutment teeth. A pontic or artificial tooth of desired shape and size is then prepared or selected and is secured to the fibers bridging the gap by an adhesive resin. After the resin has been cured by appropriate activation, the excess resin is trimmed from the pontic and surrounding teeth using finishing techniques which are common in the art.

With respect to the splinting of mobile teeth, teeth which have lost root support by peridontal disease processes which cause jaw bone resorption or bone height, move individually. If allowed to continue, tooth loss will result. By attaching the resin impregnated fibers from loose tooth to loose tooth, they are splinted together and function as a fixed, immovable unit. This is an efficient, time saving system which replaces existing techniques costing several times more. Further, with the fiber reinforced splint process described above, there is no need to cut or prepare the teeth.

One step in the above processes which is particularly important and which is often quite time consuming is the step of impregnating or saturating the fibers or fiber bundles with resin. This step commonly involves cutting a plurality of fiber bundles to the desired length, placing the fiber bundles, along with a measured amount of dispensed resin, onto a pallet or other substrate and then manually working the resin into the fiber bundles with a dental tool or the like until the fibers are fully impregnated with the resin. This is a relatively time consuming process because of the high viscosity of the resin material, the relatively limp and fine texture of the fibers and the need for the fibers to be fully impregnated. Insufficient impregnation will result in the existence of "dry" fibers. Dry fibers can act as a wick for bacteria or oral fluids which can lead to odor, decay and other future dental problems. Thus, it is extremely important to totally impregnate all the fibers with the resin so as to eliminate any dry fibers. However, despite this desired objective, it is often difficult to insure that all fibers have been fully impregnated. Accordingly, there is a need for an apparatus and method for impregnating fibers or fiber bundles with resin or the like which is less time consuming, while at the same time insuring that all the fibers or fiber bundles are fully impregnated.

SUMMARY OF THE INVENTION

In contrast to the prior art, the present invention provides an apparatus and method for fully impregnating fibers or fiber bundles with a resin or the like, and more particularly, to an apparatus and method for dispensing fully impregnated fibers or fiber bundles.

More specifically, according to the preferred embodiment, the dispenser includes a body having an interior resin containing cavity with a fiber inlet end and a fiber outlet end. The cavity is filled with an impregnating material such as a resin or the like and a fiber supply is provided for selectively feeding the unimpregnated fiber to the fiber inlet end. The fiber is then directed through the resin containing cavity where it is impregnated with resin. The fiber then exits through the outlet end as a fully impregnated fiber.

In an alternate apparatus embodiment, the fiber supply is provided within the resin containing cavity, thus dispensing with the need for a fiber inlet end.

The method of the present invention includes providing a supply of continuous fibers either within or outside a resin containing cavity. These fibers are then exposed to the resin in the cavity containing the impregnating resin and extend out through the fiber outlet. When resin impregnated fibers are desired, a desired length of such fibers are pulled from the fiber outlet and severed.

Accordingly, it is an object of the present invention to provide an improved apparatus and method for impregnating fibers or fiber bundles with a resin or the like.

Another object of the present invention is to provide an improved apparatus and method for dispensing resin impregnated fibers or fiber bundles.

A further object of the present invention is to provide an improved apparatus and method for preparing and dispensing resin impregnated fibers which is less time consuming than prior methods.

A still further object of the present invention is to provide an improved apparatus and method for preparing and dispensing resin impregnated fibers which are fully impregnated with the impregnating material and eliminate the existence of "dry" fibers. These and other objects of the present invention will become apparent with reference to the drawings, the description of the preferred embodiment and the appended claims.

DESCRIPTION OF THE DRAWINGS

FIG. 1 is a perspective, broken apart view of the preferred embodiment of the apparatus of the present invention.

FIG. 2 is a side view, partially in section, of the apparatus shown in FIG. 1.

FIG. 3 is a view, partially in section, as viewed along the section line 3—3 of FIG. 2.

FIG. 4 is a view, partially in section, as viewed along the section line 4—4 of FIG. 2.

DESCRIPTION OF THE PREFERRED EMBODIMENT

Figure 5:
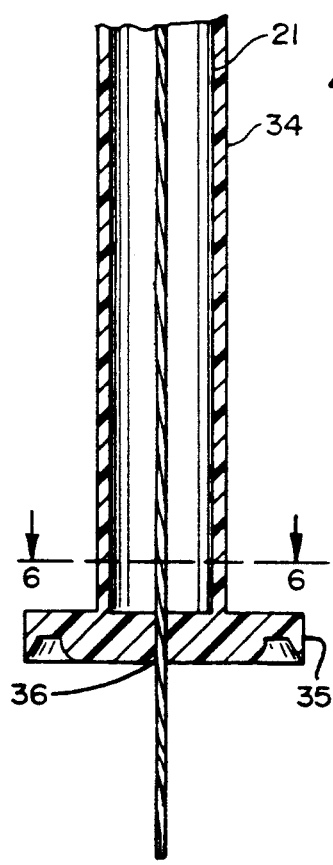
FIG. 5 is an alternate embodiment of a plunger stem for use in the embodiment of FIGS. 1 and 2.

The present invention is directed to an apparatus and method for impregnating fibers or fiber bundles with a resin or other impregnating material and/or an apparatus and method for dispensing resin impregnated fibers or fiber bundles. Throughout the application the terms "fibers" and "fiber bundles" will be used. It is intended that these terms are interchangeable and that use of the terms "fiber" or "fibers" shall mean not only a single fiber but a plurality of fibers as well as one or more fiber bundles. Further, the term "fiber" shall include all filament or thread like materials, either synthetic of natural. Still further, throughout the application the terms "resin" or "impregnating material" will be used. It is intended that these terms are also interchangeable and unless more specifically defined, the term "resin" shall be construed to mean any material which is desired to be impregnated into a fiber or a fiber bundle.

With initial reference to FIGS. 1 and 2, the apparatus of the present invention includes a dispenser or dispenser body 11, a plunger assembly 12 and a fiber supply mechanism 14. The dispenser 11 includes an interior resin containing cavity 15, a fiber outlet or fiber outlet end 16 and a fiber inlet or fiber inlet end 18. The cavity 15 is filled with a fixed supply of resin 19 or other impregnating material. Although the dispenser body 11 can be constructed with a variety of configurations, the dispenser body 11 of the preferred embodiment is in the form of a plunger type dispenser in which the resin carrying cavity 15 has a generally cylindrically shaped configuration. The side walls of the cavity 15 are connected with the fiber outlet 16 through a generally nozzle or funnel shaped side wall 20. The fiber outlet 16 has an internal diameter which is significantly less than the internal diameter of the cavity 15, but which is sufficiently large to allow the fiber or fiber bundle 21 to be manually pulled from the cavity 15. On the other hand, the opening in the outlet end 16 must be sufficiently small to prevent the resin 19 or other material within the cavity 15 from leaking through the outlet 16 without external force. The exact size of the opening in the outlet end 16 will be determined principally by the size of the fibers or fiber bundles and the viscosity of the resin 19.

The top end of the dispenser body 11 in the preferred embodiment is provided with the fiber inlet end 18 and a pair of laterally extending force resist members 22 which are intended for engagement by the user's fingers to assist in inserting the plunger assembly 12 into the dispenser body 11.

The plunger assembly 12 includes a plunger head 24 and a plunger stem 25. The plunger stem 25 is a generally elongated member having a first end integrally connected with the plunger head 24 and a second end connected with the fiber supply mechanism 14 as will be described below. The plunger head 24 is a generally disc shaped element having an outer circumferential dimension approximating the inner dimension of the resin containing cavity 15. This dimensional relationship enables the plunger, when inserted into the cavity 15, to confine the resin 19 to that part of the cavity 15 below the plunger head 24 or, if inserted with sufficient force, to actually cause the resin 19 within the cavity 15 to exit from the outlet end 16.

In the preferred embodiment, an outer edge of the plunger head 24 is provided with a small notch 26 as best illustrated in FIG. 3. The purpose of this notch 26 is to allow the unimpregnated fiber to pass the plunger head 24 and enter the cavity 15 for exposure to the resin 19. The notch 26 can have a variety of configurations; however, the preferred configuration is a linear cut or slit. As shown in FIG. 4, this causes the fibers to be spread out as they pass into the resin filled cavity 15, which in turn results in greater contact with, and impregnation by, the resin 19.

The cross sectional view of the plunger stem 25 as shown in FIG. 4 shows the stem 25 as being provided with a plurality of longitudinally extending ribs 27 which provide structural rigidity to the stem 25. With this configuration, the unimpregnated fiber passes along the side of the plunger stem 25 to the plunger head 24 as shown.

The fiber supply mechanism 14 of the preferred embodiment is illustrated best in FIGS. 1 and 2. Specifically, the mechanism 14 includes a yoke member comprising a yoke base 29 and a pair of spaced side supports 34 extending upwardly from the base 29. In the preferred embodiment, the yoke base 29 is mounted to the end of the plunger stem 25 opposite the plunger head 24. A spool 30 of unimpregnated fiber 32 is journalled within the yoke about the axle member 33. The axle member 33 is in turn supported between the side supports 34. The spool 30 is rotatably mounted on the axle 33 so that rotation of the spool 30 will result in a continuous supply of fibers 21 from the fiber supply 32. The preferred embodiment illustrated in FIGS. 1 and 2 shows the spool 30 to be freely rotatable about the axle 33; however, appropriate detent or other resist means (not shown) can be provided in conjunction with the spool 30 if desired. It is also contemplated that fiber supply means other than a spool mechanism may be utilized.

Figure 6:
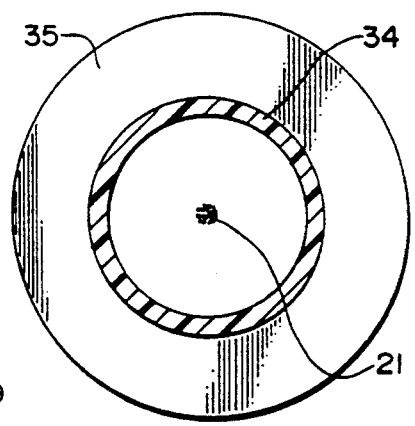
FIG. 6 is a view, partially in section, as taken along the section line 6—6 of FIG. 5.

An alternate embodiment for a plunger stem configuration is illustrated in FIGS. 5 and 6. In this embodiment, the plunger stem 34 is an elongated, generally tubular member having a hollow interior and the plunger head 35 is provided with a generally centrally positioned opening 36 through which the unimpregnated fiber 21 can pass into the resin containing chamber 15 (FIG. 2). In FIGS. 5 and 6, the central opening 36 in the plunger head 35 is shown to be generally circular; however, it could be of any shape, including a slit or cut which would cause the fibers 21 to fan out or be separated upon entering the cavity 15, thereby improving exposure to the resin. With a plunger of the configuration illustrated in FIGS. 5 and 6, the fiber 21 from the fiber supply mechanism 14 is intended to enter the top of the stem 34 through an opening in a portion of the yoke base 29.

Figure 7:
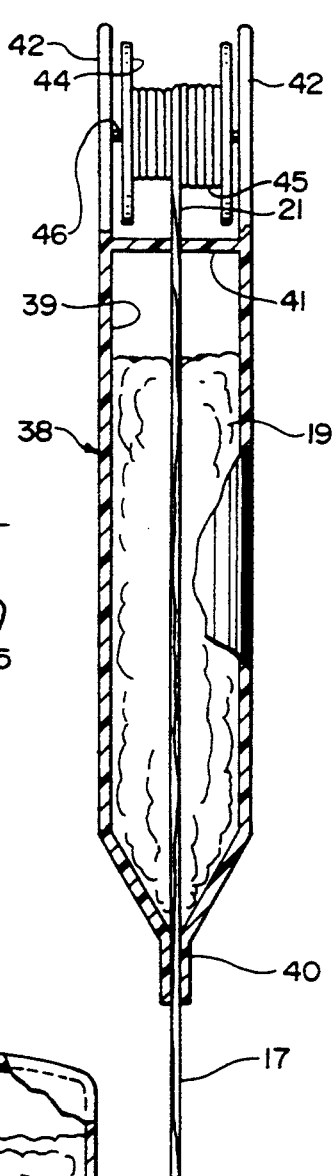
FIG. 7 is a side view, partially in section, of an alternate embodiment of an apparatus in accordance with the present invention.

A further embodiment of an apparatus in accordance with the present invention is illustrated in FIG. 7. In contrast to the embodiment of FIGS. 1–6 in which a plunger arrangement is contemplated, the embodiment of FIG. 7 contemplates that the benefits of the present invention can also be achieved without such a plunger assembly. In FIG. 7, the dispenser body 38 is provided with an internal resin receiving cavity 39, an unimpregnated fiber inlet end 41 and an impregnated fiber outlet end 40. The cavity is provided with a supply of the resin 19 in a quantity sufficient to impregnate the fiber. The end 41 is provided with an opening or slit to permit the unimpregnated fiber 21 to enter the cavity 39. A fiber supply mechanism is connected with the inlet end of the dispenser 38 and includes a pair of spaced yoke members 42 which rotatably support a spool 44 of unimpregnated fibers 45 about the axle member 46. With the embodiment of FIG. 7, it is preferable for the device to be held in a generally upright position to insure that the fibers within the cavity 39 will be in contact with the resin 19 prior to being dispensed.

Figure 8:
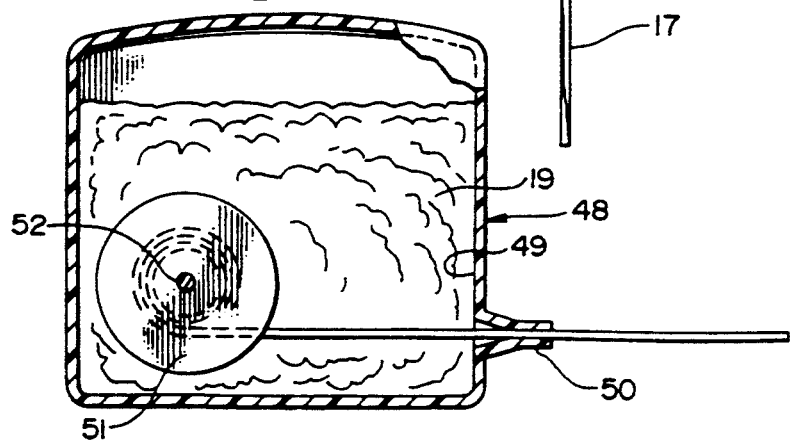
FIG. 8 is a side view, partially in section, of a further alternate embodiment of an apparatus in accordance with the present invention.

A still further embodiment of an apparatus in accordance with the present invention is illustrated in FIG. 8. In FIG. 8, the dispenser body is illustrated by reference numeral 48 and is provided with an internal resin receiving cavity 49 having a supply of resin 19. The dispenser 48 is also provided with an impregnated fiber outlet 50 with an internal opening sufficiently large to allow the impregnated fiber 17 to be pulled from the dispenser 48, but not large enough to permit the resin 19 within the cavity 49 to leak from the cavity or pass through the outlet 50 without external force. The apparatus of FIG. 8 is provided with a supply of fiber 51 which is in the form of a spool of fiber. The spool is rotatable about the axle 52 which is in turn supported within the dispenser 48. It is contemplated that a variety of means can be used to provide a supply of fiber provided within the cavity 49. In fact the fiber can merely be disposed with the resin cavity. All that is necessary is that there be a supply of fiber within the cavity 49 such that it can be freely pulled from the outlet end 50 and that while it is disposed within the cavity or as it is being pulled through the outlet end 50, it will be exposed to the impregnating resin 19 within the cavity 49.

The particular resin 19 which is provided within the dispenser cavities of the various embodiments can be any resin which is desired for impregnation of the fibers. For example, in the preferred use in connection with the field of dentistry and more specifically in connection with its use as a reinforcement in tooth replacement or stabilization procedures, the resin is a relatively high viscosity composite filling material or resin which is commonly used in the dental field. The selected resin should, of course, be capable of bonding to the tooth surfaces and to the selected fibers and also, when combined and cured with the fibers, be capable of supporting a replacement tooth between adjacent abutment teeth and withstanding the forces generated during mastication. A common composite adhesive resin having these characteristics is a resin known generically as a composite luting resin. Such a resin is manufactured by Ivoclar or Vivadent and is identified as a Fiber-Bond or Dual Cement resin. Preferably, such resins are light activated or light-polymerized and have a room temperature viscosity approximating that of cooking lard.

The fibers or fiber bundles which are to be used with the apparatus of the present invention will also be determined by the specific use to which the apparatus is put. In the preferred dental field use, the fibers comprise a bundle of fibers in which the individual fiber strands in the fiber bundle preferably have diameters quite small, while still having relatively large tensile strength. Fibers or fiber bundles referred to generically as polyethylene or polypropylene fibers are examples of fibers which may be used. The preferred fibers are polypropylene fibers. Fibers such as those known by the trademark KEVLAR may also be used. Glass fibers, including "s" glass and "E" glass may also be used. Examples include the resins manufactured by Glasspan Inc.

Having described the structure of the present invention in detail, the use of such apparatus and the method of the present invention can be described as follows.

With respect to the embodiment of FIGS. 1–4, and also the embodiment of FIGS. 5 and 6, the unimpregnated fiber 21 extends from the fiber supply mechanism 14, past the plunger head 24 (FIGS. 1–4) or 35 (FIGS. 5 and 6) and into the interior cavity 15. Here the fibers are exposed to, and impregnated with, the resin 19. When a length of impregnated fiber is desired, the user grips the end of the impregnated fiber 17 extending from the outlet end 16 with a gripping member such as a pliers and pulls a desired length of impregnated fibers from the outlet 16. Such length of fibers can then be cut. Because of the nature of the fibers, this is commonly accomplished with a hot cutting blade rather than a scissors or a knife. The dispensed, impregnated fiber length is then ready for desired use and application. As the impregnated fibers 17 are pulled from the dispenser 11 in FIGS. 1–4, the plunger assembly 12 tends to be pulled downwardly into the cavity 15 as the impregnated fiber is pulled through the outlet 16. This movement of the plunger assembly 12 results from the unimpregnated fibers 21 being pulled through the slit 26 of FIG. 3 or the hole 36 of FIGS. 5 and 6. Because of this movement of the plunger, that portion of the cavity 15 below the plunger head 24 (FIGS. 1 and 2) or 35 (FIG. 5) is always assured of being filled with resin 19. This, in turn, insures total impregnation of the fiber.

The embodiment of FIG. 7 functions similarly, except that it is not provided with a plunger mechanism. Instead, the unimpregnated fiber 21 extends through the opening in the end 41 into the interior of the cavity 39 for impregnation exposure with the resin 19 contained therein. With this embodiment, because of the fact that the resin 19 may not completely fill the cavity 39 in this particular embodiment, it is preferable for the device to be maintained in a generally upright position as shown.

The embodiment of FIG. 8 functions similar to the other embodiments except that the supply of fiber is positioned internally within the resin containing cavity 49. In both of the embodiments of FIGS. 7 and 8, a desired length of impregnated fiber is pulled from the fiber outlet and severed.

Although the description of the preferred embodiment has been quite specific, it is contemplated that various modifications could be made without deviating from the spirit of the present invention. Accordingly, it is intended that the scope of the present invention be dictated by the appended claims rather than by the description of the preferred embodiment.

We claim:

1. A dental fiber dispenser apparatus for dispensing impregnated fibers comprising:

a dispenser body having a closed impregnating material cavity, said cavity having an impregnated fiber outlet in communication with said cavity and being free of openings except for said fiber outlet, a fixed supply of impregnating material comprising a polymerizable resin disposed within said cavity, said cavity being free of any impregnating material inlet;

a supply of fiber wherein said fiber is a fiber bundle comprised of a plurality of fibers exposed to said impregnating material within said cavity and having one end extending through said fiber outlet wherein said supply of fiber is disposed entirely within said cavity, the size of said fiber outlet, the size of said fiber and the viscosity of said impregnating material being such as to prevent said impregnating material from flowing through said fiber outlet without the application of external force.

2. A hand held, manually operable apparatus for dispensing impregnated fibers comprising:

a dispenser body having a closed impregnating material cavity, said cavity having an impregnated fiber outlet in communication with said cavity wherein said cavity includes both a fiber outlet and a fiber inlet and said cavity is free of openings except for said fiber outlet and fiber inlet and is free of any impregnating material inlet and wherein said cavity includes a plunger end and said apparatus includes a plunger with a plunger head insertable into said plunger end for manually pressurizing said impregnating material within said cavity;

a fixed supply of impregnating material disposed within said cavity; and a supply of fiber exposed to said impregnating material within said cavity and having one end extending through said fiber outlet, the size of said fiber outlet, the size of said fiber and the viscosity of said impregnating material being such as to prevent said impregnating material from flowing through said fiber outlet without the application of external force, said supply of fiber further including a portion disposed outside said cavity whereby said fiber extends from said portion, into said fiber inlet, through said cavity and out from said fiber outlet.

3. The apparatus of claim 2 including means connected with said plunger for supporting said supply of fiber.

4. The apparatus of claim 3 wherein said means for supporting said supply of fiber includes a spool.

5. The apparatus of claim 2 wherein said supply of fiber is a fiber bundle comprised of a plurality of fibers.

* * * * *